(12) United States Patent
Peluso et al.

(10) Patent No.: US 8,314,144 B2
(45) Date of Patent: *Nov. 20, 2012

(54) COMPOUNDS HAVING ANTITUMOR ACTIVITY

(75) Inventors: Gianfranco Peluso, Benevento (IT); Menotti Calvani, Rome (IT)

(73) Assignee: Defiante Farmaceutica, S.A., Funchal-Madeira (PT)

( * ) Notice: Subject to any disclaimer, the term of this patent is extended or adjusted under 35 U.S.C. 154(b) by 117 days.

This patent is subject to a terminal disclaimer.

(21) Appl. No.: 12/683,870

(22) Filed: Jan. 7, 2010

(65) Prior Publication Data

US 2010/0227791 A1    Sep. 9, 2010

Related U.S. Application Data

(63) Continuation-in-part of application No. 10/585,972, filed as application No. PCT/EP2005/001257 on Feb. 8, 2005, now Pat. No. 7,652,066.

(30) Foreign Application Priority Data

Feb. 12, 2004   (IT) .............................. MI2004A0230

(51) Int. Cl.
    *A61K 31/27*   (2006.01)
(52) U.S. Cl. ...................... 514/476; 514/546
(58) Field of Classification Search .................. 514/476, 514/546
See application file for complete search history.

(56) References Cited

U.S. PATENT DOCUMENTS

| 6,369,073 | B1 | 4/2002 | Giannessi et al. |
| 6,444,701 | B1 | 9/2002 | Giannessi et al. |
| 6,610,699 | B2 * | 8/2003 | Cavazza et al. ............... 514/283 |
| 7,652,066 | B2 * | 1/2010 | Peluso et al. .................. 514/476 |
| 2002/0052348 | A1 | 5/2002 | Giannessi et al. |

FOREIGN PATENT DOCUMENTS

WO    99/59957    11/1999

OTHER PUBLICATIONS

Cancer Research, Zhou et al., 2003, 63:7330-7337.
Gianessi et al., 1999, CAS: 131:351673.
International Search Report of PCT/EP2005/001257, mailed May 27, 2005.

* cited by examiner

*Primary Examiner* — Rei-tsang Shiao
(74) *Attorney, Agent, or Firm* — Lucas & Mercanti, LLP

(57) ABSTRACT

Disclosed is the use of compounds of formula (I)

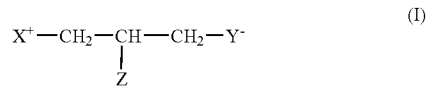

wherein X, Y and Z are as defined in the description of the invention, for the preparation of an antitumor medicament, optionally in combination with different biologically active substances.

19 Claims, 1 Drawing Sheet

COMPOUNDS HAVING ANTITUMOR ACTIVITY

This application is a continuation-in-part of U.S. application Ser. No. 10/585,972, filed Jul. 13, 2006, which is the U.S. national phase of international application PCT/EP2005/001257, filed 8 Feb. 2005, which designated the U.S. and claims priority to and the benefit of Italian Patent Application No. IT MI2004A000230, filed 12 Feb. 2004, the entire contents of each of which are hereby incorporated by reference in their entirety.

The present invention relates to a new class of compounds having antitumor activity. Specifically the invention provides the use of compounds of general formula (I):

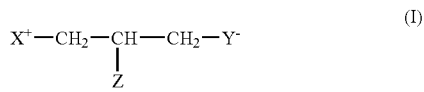

$$X^+ - CH_2 - CH - CH_2 - Y^-$$
$$\qquad\qquad | $$
$$\qquad\qquad Z$$

(I)

wherein X+ is selected from the group consisting of N+($R_1$, $R_2$, $R_3$) and P+($R_1$, $R_2$, $R_3$), wherein $R_1$, $R_2$ and $R_3$, which are the same or different, are selected from the group consisting of hydrogen and $C_1$-$C_9$ straight or branched alkyl groups, —CH=NH($NH_2$), —$NH_2$, —OH; or two or more $R_1$, $R_2$ and $R_3$, together with the nitrogen atom which they are linked to, form a saturated or unsaturated, monocyclic or bicyclic heterocyclic system; with the proviso that at least one of $R_1$, $R_2$ and $R_3$ is different from hydrogen;

Z is selected from
—$OR_4$,
—$OCOOR_4$,
—$OCONHR_4$,
—$OCSNHR_4$,
—$OCSOR_4$,
—$NHR_4$,
—$NHCOR_4$,
—$NHCSR_4$,
—$NHCOOR_4$,
—$NHCSOR_4$,
—$NHCONHR_4$,
—$NHCSNHR_4$,
—$NHSOR_4$,
—$NHSONHR_4$,
—$NHSO_2R_4$,
—$NHSO_2NHR_4$,
—$SR_4$, wherein $R_4$ is a $C_2$-$C_{20}$ saturated or unsaturated, straight or branched alkyl group;

Y— is selected from the group consisting of —COO—, $PO_3H$—, —$OPO_3H$—, tetrazolate-5-yl;

for the preparation of an antitumor medicament.

A first group of preferred compounds comprises the compounds of formula (I) wherein X is $N^+$($R_1$, $R_2$, $R_3$), more preferably trimethylammonium. A second group of preferred compounds comprises the compounds of formula (I) wherein two or more $R_1$, $R_2$ and $R_3$, together with the nitrogen atom which they are linked to, form an heterocyclic system, which is preferably selected from morpholinium, pyridinium, pyrrolidinium, quinolinium, quinuclidinium.

A third group of preferred compounds comprises the compounds of formula (I) wherein $R_1$ and $R_2$ are hydrogen and $R_3$ is selected from the group consisting of —CH=NH($NH_2$), —$NH_2$ and —OH.

Within the different embodiments of the present invention, the $R_4$ group is preferably a $C_7$-$C_{20}$ saturated or unsaturated, straight or branched alkyl group. Preferred $R_4$ groups are selected from the group consisting of heptyl, octyl, nonyl, decyl, undecyl, dodecyl, tridecyl, tetradecyl, pentadecyl, hexadecyl, heptadecyl, octadecyl, nonadecyl and eicosyl.

Preferred examples of Z group are ureido (—NHCONHR_4), and carbamate (—NHCOOR_4, —OCONHR_4).

The compounds of formula (I) wherein X+, $R_1$, $R_2$, $R_3$, have the above disclosed meanings, Z is ureido (—NHCONHR_4) or carbamate (—NHCOOR_4, —OCONHR_4), $R_4$ is a $C_7$-$C_{20}$, preferably a $C_9$-$C_{18}$ saturated or unsaturated, straight or branched alkyl group, are particularly preferred.

The compounds of formula (I) have an asymmetry center on the carbon atom bound to a Z group. For the purposes of the present invention, each compound of formula (I) can exist both as R,S racemic mixture and as separate R/S isomeric form.

The compounds of formula (I) are quaternary ammonium or phosphonium derivatives (X+) always containing a Y— anionic group. Depending on pH, each compound of formula (I) can exist indifferently as amphoion (inner salt) or as a compound wherein Y— is present in the YH form. In such a case, X+ is salified with a pharmacologically acceptable acid. Formula (I) covers all these different possibilities.

A group of particularly preferred compounds comprises:
1) R,S-4-trimethylammonium-3-(nonylcarbamoyl)-aminobutyrate;
2) R,S-4-quinuclidinium-3-(tetradecyloxycarbonyl)-oxybutyrate;
3) R,S-4-trimethylammonium-3-(nonylcarbamoyl)-oxybutyrate;
4) R,S-4-trimethylammonium-3-(nonyloxycarbonyl)-oxybutyric acid chloride;
5) R,S-4-trimethylphosphonium-3-(nonylcarbamoyl)-oxybutyrate;
6) R,S-4-trimethylammonium-3-(octyloxycarbonyl)-aminobutyrate;
7) R,S-4-trimethylammonium-3-(nonyloxycarbonyl)-amino butyrate;
8) R,S-4-trimethylammonium-3-octyloxybutyrate;
9) R,S-4-trimethylammonium-3-tetradecyloxybutyrate;
10) R,S-1-guanidinium-2-tetradecyloxy-3-(tetrazolate-5-yl)-propane;
11) R,S-1-trimethylammonium-2-tetradecyloxy-3-(tetrazolate-5-yl)-propane;
12) R,S-3-quinuclidinium-2-(tetradecyloxycarbonyl)-oxy-1-propanephosphonate monobasic;
13) R,S-3-trimethylammonium-2-(nonylaminocarbonyl)-oxy-1-propanephosphonate monobasic;
14) R,S-3-pyridinium-2-(nonylaminocarbonyl)-oxy-1-propanephosphonic acid chloride;
15) R-4-trimethylammonium-3-(tetradecylcarbamoyl)-aminobutyrate;
16) R-4-trimethylammonium-3-(undecylcarbamoyl)-aminobutyrate;
17) R-4-trimethylammonium-3-(heptylcarbamoyl)-aminobutyrate;
18) R,S-4-trimethylammonium-3-(nonylthiocarbamoyl)-aminobutyrate;
19) R-4-trimethylammonium-3-(nonylcarbamoyl)-aminobutyrate;
20) S-4-trimethylammonium-3-(nonylcarbamoyl)-aminobutyrate;
21) S-4-trimethylammonium-3-(tetradecylcarbamoyl)-aminobutyrate;
22) R,S-4-trimethylammonium-3-tetradecylaminobutyrate;
23) R,S-4-trimethylammonium-3-octylaminobutyrate;

24) R,S-4-trimethylammonium-3-(decansulfonyl)aminobutyrate;
25) R,S-4-trimethylammonium-3-(nonylsulfamoyl)aminobutyrate;
26) S-4-trimethylammonium-3-(dodecansulfonyl)aminobutyrate;
27) R-4-trimethylammonium-3-(dodecansulfonyl)aminobutyrate;
28) S-4-trimethylammonium-3-(undecylsulfamoyl)aminobutyrate;
29) R-4-trimethylammonium-3-(undecylsulfamoyl)aminobutyrate;
30) R-4-trimethylammonium-3-(dodecylcarbamoyl)aminobutyrate;
31) R-4-trimethylammonium-3-(10-phenoxydecylcarbamoyl)aminobutyrate;
32) R-4-trimethylammonium-3-(trans-b-styrenesulfonyl) aminobutyrate.

The preparation of the compounds of formula (I) is disclosed in the international patent application published under no WO 99/59957, in the name of the same applicants, which is herein incorporated by reference. Described therein is the use of the compounds (I) for the treatment of hyperglycaemic states such as diabetes and the pathologies associated therewith. The therapeutic activity of compounds (I) is attributed to an effect of carnitine palmitoyl transferase (CPT) inhibition.

In in vitro studies on different tumor cell lines, it has surprisingly been found that compounds (I) exert a remarkable antiproliferative and tumoricidal effect which is independent from CPT inhibition, as confirmed by the observation that a known CPT-1 inhibitor, etomoxir, when assayed in the same experimental conditions used for compounds (I), did not show any antiproliferative or tumoricidal activity. The in vitro results were subsequently confirmed in vivo using animal models of tumor. Also in these conditions, low dosages of compounds (I) proved efficacious in reducing the tumor mass without relevant side effects.

Accordingly, one object of the present invention is the use of compounds (I) for the preparation of an antitumor medicament.

The Diseases to be Treated

The compositions and methods of the present invention are useful for treating proliferative diseases or diseases that are associated with or triggered by persistent angiogenesis, such as neoplasms.

The term "neoplasm" indicates an abnormal mass of tissue as a result of neoplasia. Neoplasia is the abnormal proliferation of cells. The growth of this type of cells exceeds, and is uncoordinated with, that of the normal tissues around it. It usually causes a tumor. Neoplasms may be benign, pre-malignant or malignant.

Benign neoplasms include for example uterine fibroids and melanocytic nevi. They do not transform into cancer.

Potentially malignant neoplasms include carcinoma in situ. They do not invade and destroy but, given enough time, will transform into a cancer.

Malignant neoplasms are commonly called cancer. They invade and destroy the surrounding tissue, may form metastases and eventually kill the host.

A primary tumor is a tumor growing at the anatomical site, where tumor progression began and proceeded to yield this mass.

Metastasis is the spread of a disease from one organ or part to another non-adjacent organ or part. Only malignant tumor cells and infections have the established capacity to metastasize. Cancer cells can break away, leak, or spill from a primary tumor, enter lymphatic and blood vessels, circulate through the bloodstream, and be deposited within normal tissue elsewhere in the body. Metastasis is one of three hallmarks of malignancy (contrast benign tumors). Most tumors and other neoplasms can metastasize, although in varying degrees (e.g., glioma and basal cell carcinoma rarely metastasize). When tumor cells metastasize, the new tumor is called a secondary or metastatic tumor, and its cells are like those in the original tumor.

According to an embodiment of the present invention the neoplasm to be treated is a primary tumor.

According to a further embodiment of the present invention, the neoplasm to be treated is a malignant neoplasm, also called cancer, or a potentially malignant neoplasm.

The compounds of the present invention are particularly useful for treating cancers such as breast cancer; lung cancer, including non-small cell lung cancer (NSCLC) and small-cell lung cancer (SCLC); gastrointestinal cancer, including esophageal, gastric, small bowel, large bowel, rectal and colon cancer; glioma, including glioblastoma; sarcoma, such as those involving bone, cartilage, soft tissue, muscle, blood and lymph vessels; ovarian cancer; myeloma; female cervical-cancer; endometrial cancer; head and neck cancer; mesothelioma; renal-cancer; uteran; bladder and urethral cancers; leukemia; lymphoma, prostate cancer; skin cancers; and melanoma.

In particular, the inventive compositions are particularly useful for treating:

i). a breast cancer; a lung cancer, e.g., non-small cell lung cancer, including non-small cell lung cancer (NSCLC) and small-cell lung cancer (SCLC); a gastrointestinal cancer, e.g., a colorectal cancer; or a genitourinary cancer, e.g., a prostate cancer; ovarian cancer; glioma, including glioblastoma;

ii). a proliferative disease that is refractory to the treatment with other chemotherapeutics; or iii). a cancer that is refractory to treatment with other chemotherapeutics due to multidrug resistance.

In a broader sense of the invention, a proliferative disease may furthermore be a hyperproliferative condition, such as a leukemia, lymphoma or multiple myeloma. The compounds of the present invention can also be used to prevent or treat diseases that are triggered by persistent angiogenesis, such as Kaposi's sarcoma, leukemia or arthritis.

The present invention also relates to the treatment of pediatric cancers.

Examples of pediatric cancer that can treat the progress of the condition, which can be inhibited according to the present invention include for example acute lymphoblastic leukemia, acute myeloid leukemia, adrenocortical carcinoma, astrocytomas, bladder cancer, brain stem glioma, brain stem glioma, central nervous system atypical teratoid/rhabdoid cancer, brain cancer, central nervous system embryonal cancers, brain cancer, astrocytomas, craniopharyngioma, ependymoblastoma, ependymoma, childhood medulloblastoma, medulloepithelioma, pineal parenchymal cancers of intermediate differentiation, supratentorial primitive neuroectodermal cancers and pineoblastoma, breast cancer, bronchial cancers, carcinoid cancer, central nervous system atypical teratoid/rhabdoid cancer, central nervous system embryonal cancers, cervical cancer, chordoma, colorectal cancer, craniopharyngioma, ependymoblastoma, ependymoma, esophageal cancer, extracranial germ cell cancer, gastric cancer, glioma, hepatocellular (liver) cancer, hodgkin lymphoma, kidney cancer, laryngeal cancer, leukemia, acute lymphoblastic/myeloid leukemia, liver cancer, hodgkin lymphoma, non-hodgkin lymphoma, medulloblastoma, medulloepithelioma, mesothelioma, multiple endocrine neoplasia syndrome, acute myeloid leukemia, nasopharyngeal cancer, oral cancer, ovarian cancer, pancreatic cancer, papillomatosis, pineal parenchymal cancers of intermediate differentiation, pineoblastoma and supratentorial primitive neuroectodermal cancers, renal cell cancer, rhabdomyosarcoma, salivary gland cancer, sarcoma, skin cancer, gastric cancer, supratentorial primitive neuroectodermal cancers, thymoma and thymic carcinoma, thyroid cancer and vaginal cancer.

Where a cancer, a cancer disease, a carcinoma or a cancer is mentioned, also metastases in the original organ or tissue and/or in any other location are implied alternatively or in addition, whatever the location of the cancer and/or metastasis.

The following tumors are preferably treated according to the invention: leukemia, carcinoma, lymphoma, sarcoma, breast, lung, head and neck, rectum bladder cancers, colon cancer, prostate cancer and papilloma, particularly leukemia and hepatocarcinoma. The therapeutic treatment can be applied at various stages of tumor growth, proliferation and diffusion.

For use in therapy, the compounds (I) may be formulated with pharmaceutically acceptable vehicles and excipients. The compositions according to the present invention are suitable for oral, parenteral, rectal, transdermal and intralesional administration. Examples of oral and parenteral forms include capsules, tablets, granules, powders, syrups and, respectively, solutions and emulsions.

The dosage of compounds (I) may vary depending on the specific product used, on the administration route and on disease progression. For example, effective doses for compounds according to the invention can range from about 0.01 mg/kg to 2,000 mg/kg. Preferably, doses of from about 0.05 mg/kg to about 500 mg/kg are given to a patient, i.e., a mammal in need thereof in a single or multiple doses for as long as clinically required. In any case, a dosage providing a plasma concentration of active substance from 0.1 to 0.50 µM, preferably 0.5-30 µM, is generally acceptable.

A further aspect of the invention regards pharmaceutical preparations containing a compound (I) in combination with different antitumor agents, for simultaneous, separate or sequential administration to a tumor patient. Examples of antitumor agents that can be used in combination with compounds (I) include cytotoxic or cytostatic compounds, antimetabolites, hormone antagonists, alcaloids, antibiotics, in particular antracyclines, alkylating agents, peptides, agents modifying the biological response, cytokines.

The choice of the specific combination of active substances, of their dosage or administration route, depends on the tumor type, on tumor resistance to pharmacological treatment, on the patient tolerance to the treatment itself and on different variables that will be evaluated on a case by case basis.

The following non-limiting examples illustrate the invention in further detail.

EXAMPLE 1

In Vitro Inhibitory Effect on Proliferation and Proapoptotic Activity of the Compound R-4-trimethylammonium-3-(tetradecylcarbamoyl)-Aminobutyrate (ST1326) on Human Hepatocarcinoma Cells (HepG2)

The tumor cell line HepG2 was provided by ATCC (American Type Cell Culture—Mannas, Va., acc. no. HB-8065) and subsequently developed in our laboratory. The cells were cultured in complete medium, i.e. MEM added with 10% FCS, 1 mM Na-pyruvate, 2 mM L-glutamine, 0.1 mM non essential amino acids and antibiotics (penicillin/streptomycin). The medium, culture products and reagents were purchased from Hyclone-Celbio (Milan, Italy). The cells were seeded in 60 mm-diameter Petri dishes. After plating the cells were grown for 24 hours prior to their treatment.

In this experiment, increasing amounts of the test molecule were added to hemiconfluent HepG2 cells (Kogure et al., Cancer Chemother. Pharmacol., 2003; DOI. 10.1007/s); the antiproliferative and proapoptotic effects were determined at different times from cell seeding.

The experimental design in some cases provided for the addition of the test compound once the cell culture had been prepared, in other cases the cultures were exposed to the compound every 24 hours after suitably removing the conditioned medium and washing the cells with new (complete) medium. The cells were counted in a Bürker chamber after suitable dilution with a vital dye to visualize the living cells. In particular, the trypan blue exclusion method was used for cell count at 0, 24 and 48 hour treatment. At least 10 cell counts were performed for each experiment and each treatment was carried out in quadruple.

A further analysis involved cytofluorimetry utilizing propidium iodide as a marker for viable cells. The test compound was assayed vs. the CTP inhibitor etomoxir to verify whether the tumoricidal effect could be attributed to CPT-1 inhibition or involved novel mechanisms. The significant data are shown in the FIGURE.

Surprisingly, the results show that only the compound ST1326 was able to exert an in vitro antiproliferative effect associated with a significant tumoricidal activity.

In addition, assays on cell viability were carried out using flow cytofluorimetry techniques. The data reported in Table 1 refer to cells treated only once (time 0); cell mortality (24, 48 and 72 hours) was calculated as the percentage (mean±standard deviation) over 10,000 acquired events.

TABLE 1

| TREATMENT | 24 hours | 48 hours | 72 hours |
|---|---|---|---|
| Control | 9.5 ± 1.1 | 10.2 ± 0.47 | 11.78 ± 1.9 |
| Etomoxir 5 µM | 10.8 ± 1.65 | 11.8 ± 0.4 | 10.1 ± 2.1 |
| Etomoxir 20 µM | 13.04 ± 1.07 | 11.2 ± 1.3 | 11.7 ± 1.3 |
| ST1326 0.1 µM | 15.3 ± 2.1 | 27.3 ± 2.2 | 49.9 ± 1.2 |
| ST1326 5 µM | 25.78 ± 1.70 | 56.29 ± 1.51 | 93.48 ± 1.5 |
| ST1326 10 µM | 53.21 ± 1.5 | 85.10 ± 0.9 | 96.3 ± 1.1 |
| ST1326 20 µM | 88.22 ± 1.9 | 89.10 ± 0.17 | 98.51 ± 1.3 |

In further experiments the test molecule was added every 24 hours, as above described, after suitably removing the surnatants and washing the cultures with complete medium. In this case, the subsequent additions of the test molecule showed an additive effect on cell viability (Table 2). In the control, the surnatant was eliminated and complete medium alone was added to the cultures. Cell mortality (at 48 and 72 hours) was calculated as the percentage (mean±standard deviation) over 10,000 acquired events.

TABLE 2

| TREATMENT | 48 hours* | 72 hours** |
|---|---|---|
| Control | 9.3 ± 1.3 | 13.06 ± 1.5 |
| Etomoxir 5 µM | 10.17 ± 1.7 | 12.6 ± 1.1 |
| Etomoxir 20 µM | 13.9 ± 1.2 | 14.1 ± 0.9 |
| ST1326 0.1 µM | 45 ± 2.0 | 56.5 ± 1.2 |

TABLE 2-continued

| TREATMENT | 48 hours* | 72 hours** |
|---|---|---|
| ST1326 5 µM | 64.7 ± 1.7 | 89.7 ± 1.4 |
| ST1326 10 µM | 87.5 ± 2.03 | 91.3 ± 1.9 |
| ST1326 20 µM | 93.9 ± 1.03 | 98.1 ± 0.9 |

*second addition of the test molecule after eliminating the surnatant;
**third addition of the test molecule after eliminating the surnatant.

EXAMPLE 2

In Vitro Proapoptotic Activity of the Compound ST1326 on Acute Leukaemia T Cells (Jurkat)

The tumor cell line Jurkat was provided by ATCC (American Type Cell Culture—Mannas, Va., acc. No. TIB-152) and subsequently developed in our laboratory. The cells were cultured in complete medium containing RPMI 1640 added with 10% FCS (bovine fetal serum), 1 mM Na-pyruvate, 2 mM L-glutamine, 4.5 g/L glucose, 10 mM HEPES and antibiotics (penicillin/streptomycin). The medium, culture products and reagents were purchased from Hyclone-Celbio (Milan, Italy). The cells were seeded in 25 mm$^2$ flasks. After plating the cells were grown for 24 hours prior to their treatment.

The experiment was carried out by adding increasing amounts of the test molecule to hemiconfluent Jurkat cells; the proapoptotic effect was determined at different times from culture preparation.

The experimental design provided for the addition of the test compound only at the start of cell culturing, and the determination of the effects at the established times. The data on cell mortality were obtained using propidium iodide flow cytofluorimetry techniques only. The fact that those cells live suspended in culture rendered these assays extremely easy to perform.

Table 3 shows that the Jurkat cells are extremely more sensitive than HepG2 cells to the tumoricidal action of the compound. For this reason the cell mortality was determined just after 2 hour treatment and at 24, 48 and 72 hrs.

The mortality was calculated as the percentage over 10.000 acquired standard events. Since the results are almost exactly overlapping, with very low deviation in all the readings for each single experiment, the mean values of 5 cytofluorimetric readings are reported in the following Table without standard deviation.

TABLE 3

| TREATMENT | 2 hours | 24 hours | 48 hours | 72 hours |
|---|---|---|---|---|
| Control | 3% | 4% | 5% | 13% |
| ST1326 0.1 µM | 3% | 4% | 5% | 13% |
| ST1326 0.25 µM | 3% | 5% | 8% | 14% |
| ST1326 0.50 µM | 7% | 15% | 35% | 56% |
| ST1326 1.0 µM | 6% | 79% | 83% | 90% |
| ST1326 2.5 µM | 6% | 91% | 97% | 99% |
| ST1326 5.0 µM | 8% | 99% | 99% | 99% |
| ST1326 10 µM | 20% | 99% | 99% | 99% |

In addition, in order to exclude the induction of toxicity in normal PBMCs by the test molecule, viability tests were also carried out with lymphocytes taken from healthy individuals and contacted with the test compound.

The results reported in Table 4 show that the test compound after 72 hours was not toxic to PBMCs at the same doses that proved able to kill Jurkat cells.

TABLE 4

| TREATMENT | 72 hours |
|---|---|
| Control | 9% |
| ST1326 1.0 µM | 9% |
| ST1326 5.0 µM | 10% |
| ST1326 10 µM | 10% |
| ST1326 20 µM | 12% |

EXAMPLE 3

In Vitro Antagonistic Activity of Sub-Optimal Doses of ST1326 Compound on the Antineoplastic Effects of Doxorubicin on Human Hepatocarcinoma Cells (HepG2)

The tumor cell line HepG2 was provided by ATCC (American Type Cell Culture—Mannas, Va., No. HB-8065) and subsequently developed in our laboratory. The cells were cultured in complete medium containing MEM added with 10% FCS (bovine fetal serum), 1 mM Na-pyruvate, 2 mM L-glutamine, 0.1 mM non-essential amino acids and antibiotics (penicillin/streptomycin). The medium, culture products and reagents were purchased from Hyclone-Celbio (Milan, Italy). The experimental design provided for the use of ST1326 and of known antineoplastic drugs, such as doxorubicin, against which the HepG2 cells show a high resistance, to determine the agonist action of the compound. The ST compound was used at a concentration that in prior experiments proved only partially able to induce a tumoricidal effect (0.1 µM; ~50% cell mortality). In this experiment, the following compounds were added to hemiconfluent HepG2 cells in 96 well plates:
  0.25, 0.5, 5.0 µg/mL doxorubicin;
  0.1 µM ST in combination with 0.25 µg/mL doxorubicin.

After 24 hr incubation, the medium containing different concentrations of doxorubicin and the ST/doxorubicin combination was removed and the cells were washed with complete medium. After 3-day treatment, the antineoplastic effect of the test compound was determined in comparison with control cells incubated in complete medium for the same period of time.

Table 5 shows that only the highest dose of doxorubicin (5.0 µg/mL) is able to induce significant cell mortality. The addition of ST and doxorubicin at concentrations of 0.1 µM and 0.25 µg/mL, respectively, allowed to demonstrate the agonist tumoricidal effect of their combination. The cell mortality was calculated as the percentage (mean±standard deviation) over 10.000 acquired events.

TABLE 5

| TREATMENT | 3 days |
|---|---|
| Control | 10.8 ± 1 |
| Doxorubicina 0.25 µg/mL | 11.2 ± 1.5 |
| Doxorubicina 0.5 µg/mL | 22.7 ± 3.5 |
| Doxorubicina 5.0 µg/mL | 48.6 ± 4.1 |
| ST1326 0.1 µM + Doxorubicina 0.25 µg/mL | 93.2 ± 2.7 |

EXAMPLE 4

In Vivo Antineoplastic Activity of the ST1326 Compound in Rats Bearing Yoshida Tumor Male Wistar rats (Morini s.r.l.) of 190-200 g weight were maintained at 22±2° C., with a light/dark cycle of 12 hours, and were given free access to water and food (standard diet). Some rats were intraperitoneally inoculated with 10×10⁷ cells from AH-130 Yoshida ascites hepatoma (Llovera et al., Int. J. Cancer 61:138-41 (1995); kind gift from Prof. J M Argilès). 5-7 days after the inoculum, the rats developed an ascites that could be detected by macroscopic analysis of the abdomen. The paracentesis revealed the presence of approximately 80-100 ml ascitic fluid, which sometimes appeared hemorrhagic, containing on average 15-20×10⁶/ml tumor cells.

The experimental protocol provided that 7 days after ascites induction 15 animals (treated group) received 2 ml of a buffered saline containing ST (25 mg/Kg i.p.), whereas other 15 animals (control group) received the buffered saline alone. The same treatment was conducted at alternate days for one week up to a total of 4 treatments for each animal. The dosage was selected on the basis of preliminary studies in which a 6.1 µM plasma concentration of ST was achieved 5 hr after intraperitoneal administration. The animals were subsequently kept under observation for 3 weeks (follow-up), examining the ascites effusion, the presence of subcutaneous neoplastic mass in the inoculum site, and the mortality.

The most interesting observation was that the treated animals survived during the 3-week follow-up period, whereas the control rats died between the first and the second week.

The post-mortem examination of the control animals showed the presence of ascitic fluid containing tumor cells in the abdominal cavity, hyperplasia of intestinal Peyer plaques, absence of tumor lesions involving the abdominal organs and finally the development of a tumor lesion close to the muscle fascia in the site of inoculum of the neoplastic cells. The treated rats were sacrificed at the end of the third week and their post-mortem examination failed to reveal any alteration in the abdominal cavity, or the presence of tumor cells in the ascitic fluid or in the inoculum site.

A synopsis of the experimental data/results is shown in the following Tables 6 and 7.

TABLE 6

|  | Survival at 1 week follow-up | Survival at 2 week follow-up | Survival at 3 week follow-up |
|---|---|---|---|
| No. of survived animals treated with buffered saline (No) | 11 | 1 | 0 |
| No. of survived animals treated with ST1326 | 15 | 15 | 15 |

TABLE 7

|  | Presence of tumor cells in the abdominal cavity (post-mortem examination) | Presence of tumor mass in the inoculum site | Presence of cachexy |
|---|---|---|---|
| No. of animals treated with buffered saline | 15 | 10 | 15 |
| No. of animals treated with ST1326 | 0 | 0 | 1 |

The experimental results obtained with oral and i.v. administration showed the efficacy of the treatment at different dosages of the test compound (oral route: 100 mg/Kg; i.v.: 2 mg/Kg).

BRIEF DESCRIPTION OF THE FIGURE

The data relating to cell viability are expressed as percentage on the number of viable cells from control cultures (=100%). (E=etomoxir; ST1326=tested compound). A remarkable reduction in the number of cells cultured in the presence of less than 10 µM ST was observed just after 24 hours. At the same concentrations etomoxir was ineffective.

The invention claimed is:

1. A method of treating a patient having colon cancer, prostate cancer or papilloma comprising administering to the patient in need thereof an effective amount of a compound of general formula (I):

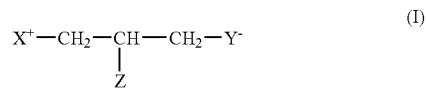

(i) wherein X⁺ is selected from the group consisting of N⁺(R₁, R₂, R₃) and P⁺(R₁, R₂, R₃), wherein R₁, R₂ and R₃, which are the same or different, are selected from the group consisting of hydrogen and $C_1$-$C_9$ straight or branched alkyl groups, —CH═NH(NH₂), —NH₂, and —OH; with the proviso that at least one of R₁, R₂ and R₃ is not hydrogen;

(ii) Z is selected from
—OR₄,
—OCOOR₄,
—OCONHR₄,
—OCSNHR₄,
—OCSOR₄,
—NHR₄,
—NHCOR₄,
—NHCSR₄,
—NHCOOR₄,
—NHCSOR₄,
—NHCONHR₄,
—NHCSNHR₄,
—NHSOR₄,
—NHSONHR₄,
—NHSO₂R₄,
—NHSO₂NHR₄, and
—SR₄,
wherein R₄ is a $C_2$-$C_{20}$ saturated or unsaturated, straight or branched alkyl group;

(iii) Y— is selected from the group consisting of —COO—, PO₃H—, —OPO3H—, tetrazolate-5-yl;
a salt, enantiomer or racemic mixture thereof.

2. The method according to claim 1, wherein in the compound of formula (I), independently of one another,
X is trimethylammonium or a group N⁺(R₁, R₂, R₃)
R₄ is selected from heptyl, octyl, nonyl, decyl, undecyl, dodecyl, tridecyl, tetradecyl, pentadecyl, hexadecyl, heptadecyl, octadecyl, nonadecyl and eicosyl;
Z is a ureido (—NHCONHR₄) or carbamate (—NHCOOR₄, —OCONHR₄) group.

3. The method according to claim 2 wherein the compound is selected from the group consisting of
R,S-4-trimethylammonium-3-(nonylcarbamoyl)-aminobutyrate;
R,S-4-quinuclidinium-3-(tetradecyloxycarbonyl)-oxybutyrate;
R,S-4-trimethylammonium-3-(nonylcarbamoyl)-oxybutyrate;

R,S-4-trimethylammonium-3-(nonyloxycarbonyl)-oxybutyric acid chloride;
R,S-4-trimethylphosphonium-3-(nonylcarbamoyl)-oxybutyrate;
R,S-4-trimethylammonium-3-(octyloxycarbonyl)-aminobutyrate;
R,S-4-trimethylammonium-3-(nonyloxycarbonyl)-amino butyrate;
R,S-4-trimethylammonium-3-octyloxybutyrate;
R,S-4-trimethylammonium-3-tetradecyloxybutyrate;
R,S-1-guanidinium-2-tetradecyloxy-3-(tetrazolate-5-yl)-propane;
R,S-1-trimethylammonium-2-tetradecyloxy-3-(tetrazolate-5-yl)-propane;
—R,S-3-quinuclidinium-2-(tetradecyloxycarbonyl)-oxy-1-propanephosphonate monobasic;
—R,S-3-trimethylammonium-2-(nonylaminocarbonyl)-oxy-1-propanephosphonate monobasic;
R,S-3-pyridinium-2-(nonylaminocarbonyl)-oxy-1-propanephosphonic acid chloride;
R-4-trimethylammonium-3-(tetradecylcarbamoyl)-aminobutyrate;
R-4-trimethylammonium-3-(undecylcarbamoyl)-aminobutyrate;
R-4-trimethylammonium-3-(heptylcarbamoyl)-aminobutyrate;
R,S-4-trimethylammonium-3-(nonylthiocarbamoyl)-aminobutyrate;
R-4-trimethylammonium-3-(nonylcarbamoyl)-aminobutyrate;
S-4-trimethylammonium-3-(nonylcarbamoyl)-aminobutyrate;
S-4-trimethylammonium-3-(tetradecylcarbamoyl)-aminobutyrate;
R,S-4-trimethylammonium-3-tetradecylaminobutyrate;
R,S-4-trimethylammonium-3-octylaminobutyrate;
R,S-4-trimethylammonium-3-(decansulfonyl)aminobutyrate;
R,S-4-trimethylammonium-3-(nonylsulfamoyl)aminobutyrate;
S-4-trimethylammonium-3-(dodecansulfonyl)aminobutyrate;
R-4-trimethylammonium-3-(dodecansulfonyl)aminobutyrate;
S-4-trimethylammonium-3-(undecylsulfamoyl)aminobutyrate;
R-4-trimethylammonium-3-(undecylsulfamoyl)aminobutyrate;
R-4-trimethylammonium-3-(dodecylcarbamoyl)aminobutyrate;
R-4-trimethylammonium-3-(10-phenoxydecylcarbamoyl)aminobutyrate;
R-4-trimethylammonium-3-(trans-b-styrenesulfonyl)aminobutyrate.

4. The method according to claim 1, wherein the compound is R-4-trimethylammonium-3-(tetradecylcarbamoyl)-aminobutyrate.

5. The method according to claim 1, wherein a colon cancer patient is treated.

6. The method according to claim 1, wherein a prostate cancer patient is treated.

7. The method according to claim 1, wherein a papilloma patient is treated.

8. The method according to claim 1, wherein said effective amount ranges from about 0.01 mg/kg to 2,000 mg/kg of said compound of formula (I).

9. The method according to claim 8, wherein said effective amount ranges from about 0.05 mg/kg to about 500 mg/kg.

10. A method of treating a patient having leukemia, lymphoma, carcinoma, sarcoma, breast cancer, lung cancer, head and neck cancer, rectal cancer, bladder cancer, colon cancer, prostate cancer or papilloma, comprising administering to the patient in need thereof an effective compound of general formula (I):

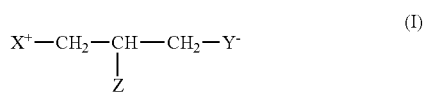

(i) wherein $X^+$ is selected from the group consisting of $N^+(R_1, R_2, R_3)$ and $P^+(R_1, R_2, R_3)$, wherein two or more of $R_1$, $R_2$ and $R_3$, together with the nitrogen atom which they are linked to, form a saturated or unsaturated, monocyclic or bicyclic heterocyclic system; with the proviso that at least one of $R_1$, $R_2$ and $R_3$ is not hydrogen;

(ii) Z is selected from
—$OR_4$,
—$OCOOR_4$,
—$OCONHR_4$,
—$OCSNHR_4$,
—$OCSOR_4$,
—$NHR_4$,
—$NHCOR_4$,
—$NHCSR_4$,
—$NHCOOR_4$,
—$NHCSOR_4$,
—$NHCONHR_4$,
—$NHCSNHR_4$,
—$NHSOR_4$,
—$NHSONHR_4$,
—$NHSO_2R_4$,
—$NHSO_2NHR_4$,
—$SR_4$,
wherein $R_4$ is a $C_2$-$C_{20}$ saturated or unsaturated, straight or branched alkyl group;

(iii) Y— is selected from the group consisting of —COO—, $PO_3H$—, —$OPO3H$—, tetrazolate-5-yl;

a salt, enantiomer or racemic mixture thereof.

11. The method according to claim 10 of a compound of formula (I), wherein, independently of one another,
X is a group $N^+(R_1, R_2, R_3)$ wherein two or more of $R_1$, $R_2$ and $R_3$, together with the nitrogen atom which they are linked to, form a heterocyclic system, which is selected from morpholinium, pyridinium, pyrrolidinium, quinolinium and quinuclidinium;
$R_4$ is selected from heptyl, octyl, nonyl, decyl, undecyl, dodecyl, tridecyl, tetradecyl, pentadecyl, hexadecyl, heptadecyl, octadecyl, nonadecyl and eicosyl;
Z is a ureido (—$NHCONHR_4$) or carbamate (—NH-$COOR_4$, —$OCONHR_4$) group.

12. The method according to claim 11 of a compound which is selected from the group consisting of
R,S-4-quinuclidinium-3-(tetradecyloxycarbonyl)-oxybutyrate;
—R,S-3-quinuclidinium-2-(tetradecyloxycarbonyl)-oxy-1-propanephosphonate monobasic;
R,S-3-pyridinium-2-(nonylaminocarbonyl)-oxy-1-propanephosphonic acid chloride.

13. The method according to claim 10, wherein a hepatocarcinoma patient is treated.

14. The method according to claim 10, wherein a leukemia patient is treated.

15. The method according to claim 10, wherein a colon cancer patient is treated.

16. The method according to claim 10 wherein a prostate cancer patient is treated.

17. The method according to claim 10 wherein a papilloma patient is treated.

18. The method according to claim 10, wherein said effective amount said effective amount ranges from about 0.01 mg/kg to 2,000 mg/kg of said compound of formula (I).

19. The method according to claim 18, wherein said effective amount ranges from about 0.05 mg/kg to about 500 mg/kg.

* * * * *